United States Patent [19]

Wittwer et al.

[11] Patent Number: 4,790,881

[45] Date of Patent: Dec. 13, 1988

[54] MOLDED HYDROPHILIC POLYMER

[75] Inventors: Fritz Wittwer, Lupsingen; Ivan Tomka, Lenzburg, both of Switzerland

[73] Assignee: Warner-Lambert Company, Morris Plains, N.J.

[21] Appl. No.: 18,651

[22] Filed: Apr. 17, 1987

Related U.S. Application Data

[63] Continuation-in-part of Ser. No. 362,177, Mar. 26, 1982, abandoned, which is a continuation-in-part of Ser. No. 698,264, Feb. 5, 1985, Pat. No. 4,655,840.

[51] Int. Cl.4 .................................................. C08L 1/08
[52] U.S. Cl. ...................................... 106/189; 106/199; 106/206; 106/208; 106/210; 106/211; 106/212; 106/213; 524/37; 524/42; 524/43; 524/376; 524/377; 524/394; 524/548

[58] Field of Search ....................... 424/451, 461, 463; 106/189, 210–213, 197, 199, 210, 211, 212, 213, 208, 206; 524/37, 42, 43, 376, 377, 394, 548

[56] References Cited

U.S. PATENT DOCUMENTS

| | | | |
|---|---|---|---|
| 2,602,755 | 7/1952 | Silvernail | 106/189 |
| 3,117,014 | 1/1964 | Klug | 106/213 |
| 3,493,407 | 2/1970 | Greminger | 106/189 |
| 4,076,846 | 2/1978 | Nakatsuka et al. | 426/62 |
| 4,369,308 | 1/1983 | Trubiano | 106/213 |
| 4,655,840 | 4/1987 | Wittwer et al. | 106/130 |
| 4,673,438 | 6/1987 | Wittwer et al. | 106/213 |

*Primary Examiner*—Theodore Morris
*Attorney, Agent, or Firm*—Howard Olevsky

[57] ABSTRACT

A moldable non gelatin containing hydrophilic polymer composition containing between 5 and 25% water.

7 Claims, 8 Drawing Sheets

MOLDED HYDROPHILIC POLYMER

CROSS REFERENCE TO RELATED APPLICATIONS

This is a continuation in part of patent application U.S. Ser. No. 362,177 filed Mar. 26, 1982 now abandoned, and a continuation in part of U.S. Ser. No. 698,264 filed Feb. 5, 1985, now U.S. Pat. No. 4,655,840.

BACKGROUND OF THE INVENTION

A. Field of the Invention

The present invention relates to a moldable hydrophilic polymer composition, for use in a molding device preferably an injection molding device.

When in the following description the term is used hydrophilic polymers are polymers with molecular masses from approximately $10^3$ to $10^7$ Dalton carrying molecular groups in their backbone and/or in their side chains and capable of forming and/or participating in hydrogen bridges. Such hydrophilic polymers exhibit in their water adsorption isotherm (in the temperature range between approximately 0° to 200° C.) an inflection point close to the water activity point at 0.5. Hydrophilic polymers are distinguished from the group called hydrocolloids by their molecular dispersity. For the maintenance of the molecular dispersity of said hydrophilic polymers, a fraction of water—according to the working range of the present invention—of 5 to 25% by weight of said hydrophilic polymers must be included; provided that the temperature of said hydrophilic polymers is in the working range between 50° C. and 190° C. of the present invention.

There are other hydrocolloids, not hydrophilic polymers in the sense of this definition, which contain more or less spherical or fibrous particles whereby those particles are composed of several macromolecules of hydrophilic polymer within the molecular mass range of $10^3$–$10^7$ Dalton giving rise to particle sizes between 0.01–10 microns which is the typical range of colloidal particles. It is a primary object of the present invention to utilize hydrophilic polymer compositions in the production of capsules.

B. Description of the Prior Art

Capsule-making machines have been developed to utilize dip-molding technology. Such technology involves the dipping of capsule-shaped pins into a gelatin solution, removing the pins from the solution, drying of the gelatin upon the pins, stripping off the gelatin capsule parts from the pins, adjusting for length, cutting, joining and ejecting the capsules. Prior art capsule-making machines have utilized the combination of mechanical and pneumatic elements to perform these functions at speeds up to about 1,200 size 0 capsules per minute. While the above described apparatus is in general suitable for the intended purposes, it is desirable to produce capsules at considerably high speed, over 15,000 size 0 capsules per minute, while at the same time precisely controlling the properties of the gelatin in order to produce the capsules hygienically and with minimum dimensional deviations so that the capsules can be filled on high speed equipment.

A prerequisite for any material to be moldable by an injection process is its ability to pass a glass transition point at a temperature compatible with the thermal stability of the material and the technical possibilities of an injection molding device.

Shirai et al. in U.S. Pat. No. 4,216,240 describes an injection molding process to produce an oriented fibrous protein product. The fibrous product as obtained by this process, differs fundamentally from the transparent glass like material of the capsules obtained from the present invention. Furthermore to obtain a flowable mass for the molding process, the protein mixtures used by Shirai et al. have to be denatured and thus lose their capacity to undergo dissolution.

Nakatsuka et al. in U.S. Pat. No. 4,076,846 uses binary mixtures of starch with salts of protein materials to obtain an edible shaped article by an injection molding process. With the present invention shaped articles from protein material, preferably gelatin and other hydrophilic polymers can be produced without the addition of starch.

Heusdens et al. in U.S. Pat. No. 3,911,159 discloses the formation of filamentous protein structures to obtain edible products of improved tenderness. With the present invention shaped articles are produced without a filamentous protein structure.

The use of an injection molding device for producing capsules of gelatin and other moldable hydrophilic polymers with similar properties is new and has not been suggested in the technical literature.

The present invention distinguishes from the known as described above, by the nature of the compositions and by the recognition that gelatin and other hydrophilic polymers possess a dissolution point within a temperature range usable for an injection molding process, provided the water content of the gelatin and other hydrophilic polymers lies within a characteristic range, giving allowance to avoid any essential drying or humidification processes of the capsules.

SUMMARY OF THE INVENTION

The present invention covers an improved hydrophilic polymer composition, for use in an improved automatic injection molding device combined with a microprocessor to control the optimum time, temperature, pressure and water content of the composition informed shaped parts. The composition has a molecular mass range of 10,000 to 2,000,000 Dalton or a molecular mass range 10,000 to 2,000,000 and 10,000,000 to 20,000,000 Dalton.

The composition has a water content range of approximately 5 to 25% by weight.

BRIEF DESCRIPTION OF THE DRAWINGS

The invention both as to its organization and method of operation together with the advantages thereof will best be understood by reference to the following specifications and taken in conjunction with the accompanying drawings.

DETAILED DESCRIPTION OF THE PREFERRED EMBODIMENT

Figure 1:
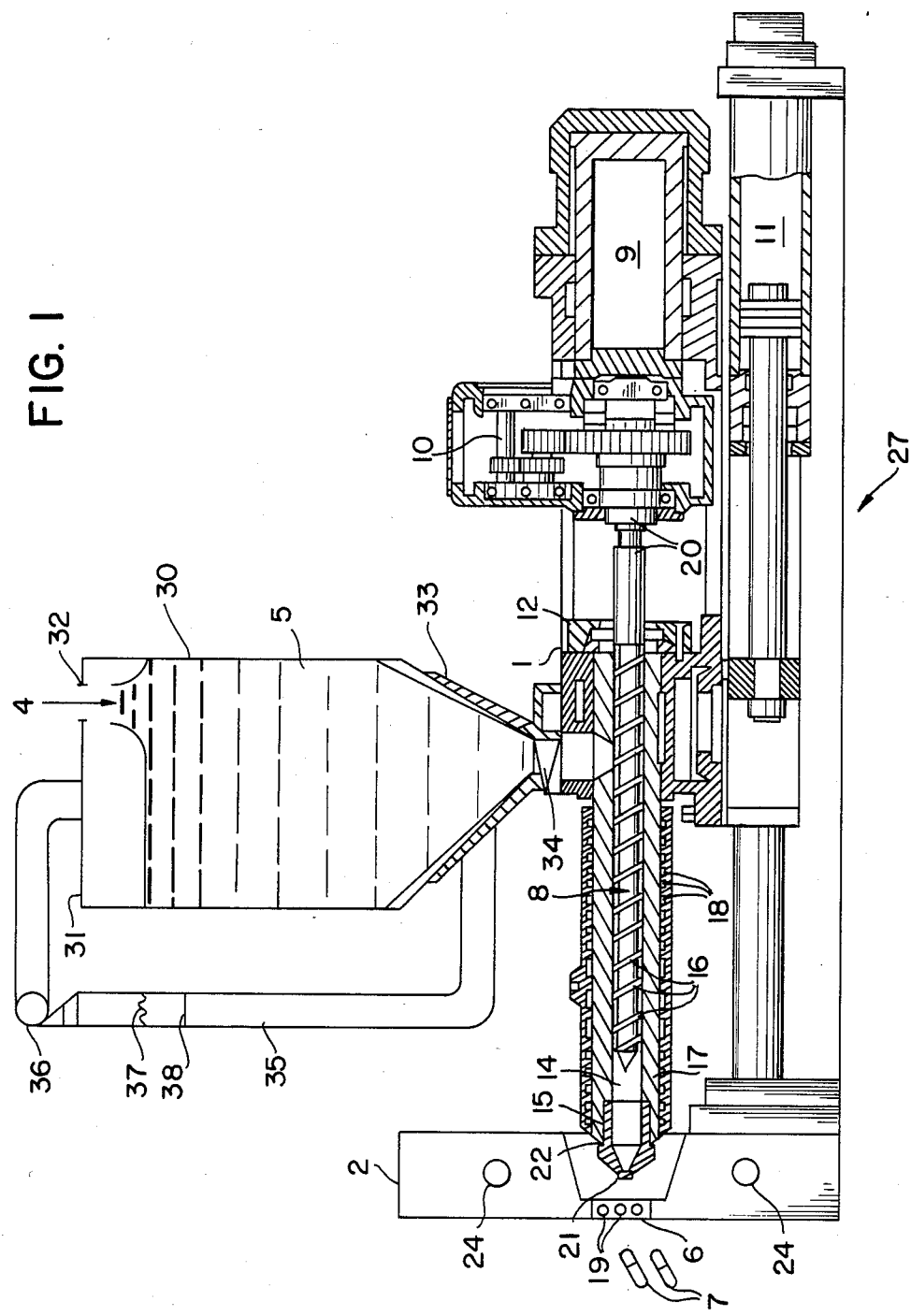
FIG. 1 is a layout of the reciprocating screw injection molding device for making capsule parts.

Referring now to FIG. 1 the injection molding device 27 generally consists of three units: a hopper unit 5, an injection unit 1 and a molding unit 2.

The function of the hopper unit 5 is receiving, storing maintaining and feeding the hydrophilic polymer 4 at a constant temperature and at a constant water content. The hopper unit 5 comprises a vertical cylinder 30 having a closed top 31 which an inlet 32 therein to receive the hydrophilic polymer 4. At the bottom of the vertical cylinder 30 is a closed conical funnel 33 and a discharge outlet 34 to feed the hydrophilic polymer 4 into an inlet 34 of the injection unit 1. There is an air duct 35 communicating between the closed top 31 and the conical funnel 33 wherein air is circulated by a blower 36, the air temperature is maintained by a thyristor 37 and the air relative humidity is maintained by a stream injector 38.

The function of the injection unit 1 is melting, dissolving in water, and plasticizing in the extruder barrel 17 the gelatin 4 fed from the hopper unit 5 into the extruder inlet 54 and injecting the plasticized hydrophilic polymer 14 into the molding unit 2.

The function of the molding unit 2 is automatically holding, opening and closing the mold 6 having capsule shaped cavities 19 therein, and ejecting the capsule parts 7 therefrom.

Within the injection unit 1 the screw 8 both rotates and undergoes axial reciprocal motion. When the screw 8 rotates, it performs the functions of melting, dissolving water, and plasticizing the hydrophilic polymer 4. When the screw 8 rotates, it performs the functions of melting, dissolving in water, and plasticizing the hydrophilic polymer 4. When the screw 8 moves axially, it performs the function of injecting by transporting and ramming the hydrophilic polymer 14 into the mold 6. The screw 8 is rotated by a variable-speed hydraulic motor and drove 10, and its axial motion is reciprocated by a duplex hydraulic cylinder 9.

Compression of the plasticized hydrophilic polymer 14 in front of the rotating screw 8 forces back the screw assembly 20 containing the screw 8, the drive 10 and the cylinder 9. When the screw assembly 20 reaches a presetback position a limit switch 12 is contacted. When a defined time has elapsed during which the hydrophilic polymer 4 becomes fully plasticized the hydraulic cylinder 11 brings the screw assembly 20 forward and uses the screw 8 as a ram for the plasticized hydrophilic polymer 14 to be injected through a valve body assembly 50 (FIG. 4) including a one-way valve 15, a needle valve 23, nozzle 22 and an outlet port 21 into the molding unit 2. The one-way valve 15 prevents the plasticized hydrophilic polymer 14 from going back over the helical flutes 16 of the screw 8. The extruder barrel 17 has steam heating coils 18 to heat the gelatin 4 while it is being compressed by the screw 8 into hydrophilic polymer plasticized 14. It is desirable for the plasticized hydrophilic polymer 14 to be heated at the lowest possible temperature and to be transported with the lowest possible temperature and to be transported with the lowest possible speed of the screw 8. The speed of the screw 8 and the heating of the plasticized hydrophilic polymer 14 within the extruder barrel 17 by the steam heating coils 18 control the quality and the output rate of the plasticized hydrophilic polymer 14 injected into the molding unit 2. The molding unit 2 holds the mold 6 having capsule shaped cavities 19 into which the plasticized polymer 14 is injected and maintained under pressure. Refrigerant cooling conduits 24 encirle the mold 6 so that when the plasticized gelatin 14 in the model 6 has cooled and sufficiently solidified, the molding unit 2 opens, the mold 6 separates and the capsule parts 7 are ejected.

Figure 2:
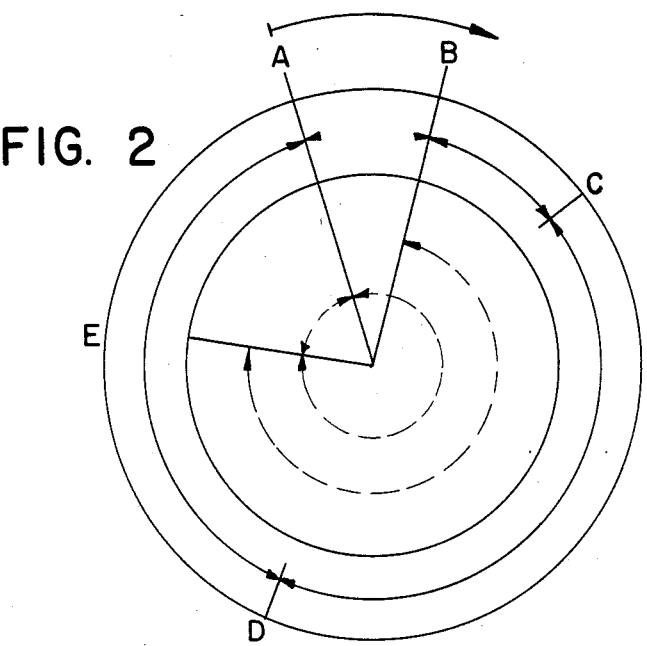
FIG. 2 is a schematic of the injection molding work cycle for making capsule parts.

Referring now to FIG. 1 and also to FIG. 2 which depicts the injection molding work cycle for the polymer 4 (containing approximately 17% water by weight) plotted against time. In general the work cycle of polymer 4 is as follows in the injection molding device 27 of the present invention:

a. Polymer 4 is fed into the hopper unit 5 where it is received, stored and maintained under condition of temperature ranging from ambient to 100° C., pressure ranging from $1-5\times10^5$ Newtons per square meter $(N\times m^{-2})$ and water content ranging from 5 to 25% by weight of the of the polymer.

b. the stored polymer is melted under controlled condition of temperature ranging from 50° to 190° C., water content ranging from 5 to 25% by weight of gelatin and pressure ranging from 600 to $3000\times10^5 N\times m^{-2}$, c. the molten polymer is dissolved in water under controlled conditions of temperature ranging from 50° to 190° C. pressures ranging from 600 to $3000\times10^5 N\times m^{-2}$ and water content ranging from 5 to 25% by weight of polymer.

d. the dissolved polymer is plasticized under controlled conditions of temperature ranging from 50° to 190° C., pressure ranging from 600 to $3000\times10^5 N\times m^{-2}$ and water content ranging from 5 to 25% by weight of gelatin.

e. the plasticized polymer is injected into the mold 6 under controlled conditions of temperature below 50° C., injection pressure ranging from 600 to $3000\times10^5 N\times m^{-2}$ and a clamping force of the mold 6 below approximately 600,000 Newton, and f. the capsule-shaped parts 7 are ejected from the molded polymer within the mold 6.

Beginning at point A of FIG. 2 the screw 8 moves forward and fills the mold 6 with plasticized polymer 14 until Point B and maintains the injected plasticized polymer 14 under high pressure during what is called the hold time from point B until Point C of FIG. 2. At Point A the one-way valve 15 at the end of the screw 8 prevents the plasticized polymer 14 from flowing back from the nozzle 22 onto the screw 8. During hold time, additional plasticized polymer 14 is injected, offsetting contraction due to cooling and solidification of the plasticized polymer 14. Later, the outlet port 21, which is a narrow entrance to the molding unit 2 closes, thus isolating the molding unit 2 from the injection unit 1. The plasticized polymer 14 within the mold 6 is still at high pressure. As the plasticized polymer 14 cools and solidifies, pressure drops to a level that is high enough to ensure the absence of sink marks, but not so high that it becomes difficult to remove the capsule parts 7 from the capsule-shaped cavities 19 within the mold 6. After the outlet port 21 closes, at Point C, screw 8 rotation commences. The plasticized polymer 14 is accommodate in the increased cylindrical space in front of the screw 8 created by its backward axial motion until Point d. The flow rate of the plasticized polymer 14 is controlled by the speed of the screw 8 and the pressure is controlled by the back pressure (i.e., the hydraulic pressure exerted on the screw assembly 20) which in turn determines the pressure of the plasticized gelatin 14 at the nozzle 22 in front of the screw 8. After plasticized polymer 14 generation for the next shot into the mold 6, the screw 8 rotation ceases at Point D. The polymer 4 on stationary screw 8 rotation ceases at Point D. The polymer 4 on the stationary scew 8 continues to melt from Points D to E by heat conduction from the steam heating coils 18 on the extruder barrel 17. This period is called soak time. Meanwhile, the solidified capsule parts 7 are ejected from the mold 6. Thereafter, the mold 6 closes to accept the next shot of polymer gelatin 14. All of these operations are automated and controlled by a microprocessor as hereinafter described.

Figure 3:
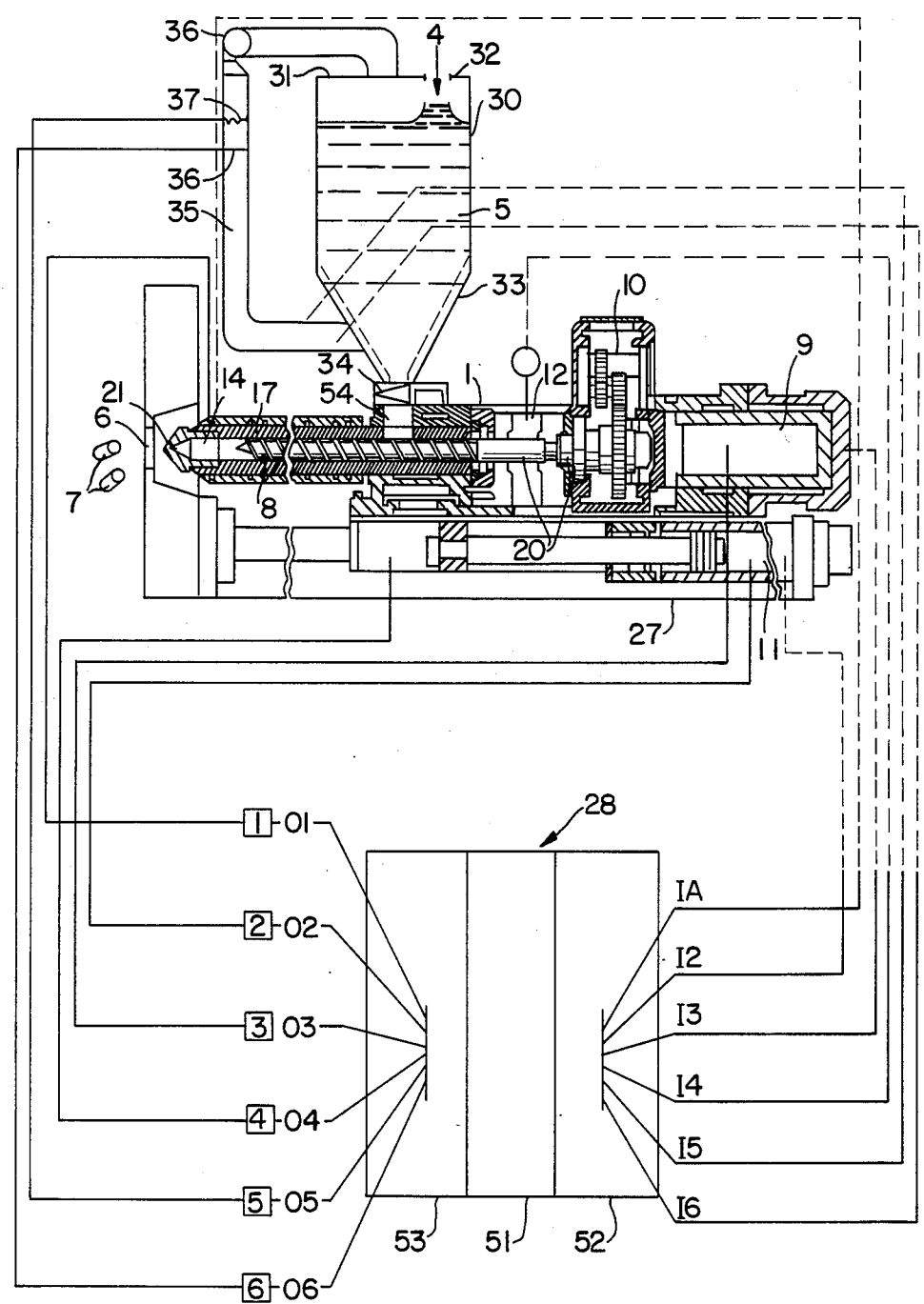
FIG. 3 is a schematic of the combined injection device microprocessor apparatus for capsule parts.

Referring now to FIG. 2 and also to FIG. 3. The injection molding work cycle of FIG. 2 is accomplished on the injection molding device 27 of FIG. 3 by hydraulic and electrical components and the corresponding circuits controlled by the mircoprocessor 28 of FIG. 3.

Through the use of solid-state circuitry and speed, temperature, limit and pressure switches fro the electric and hydraulic systems, the microprocessor 28 of the present invention utilized command signals in its memory 51 fro the parameters of time, temperature and pressure condition of the Table 1 below for the injection molding work cycle of FIG. 2 to be accomplished by the injection molding device 27 of FIG. 3 in producing gelatin capsule parts 7.

Starting at molding cycle Point A in FIG. 2, the injection molding work cycle operates as follows:

When sufficient plasticized gelatin 14 has accumulated in front of the screw 8 (microprocessor time controlled) and also when the screw assembly 20 carrying the screw 8, drive 10 and hydraulic motor 9 has been pushed far enough backwards against a constant back-pressure as controlled by control circuit 3, limit switch 12 will be actuated by position sensing circuit 14. Upon these two conditions control circuit 4 is actuated causing the hydraulic fluid to flow into the forward portion of the hydraulic cylinder 11. This rams the screw assembly 20 forward injecting the plasticized polymer 14 into the mold 6 as molding cycle Point B of FIG. 2 is reached, and, as controlled by the microprocessor 28, the screw 8 remains stationary in this forward position under high pressure for certain period of time until Point C.

From molding cycle Point B of FIG. 2 onwards the plasticized polymer 14 cools down in the mold 6 and the port 21 closes at molding cycle Point C of FIG. 2.

At molding cycle Point C of FIG. 2, the screw 8 starts to rotate again and the hydraulic pressure reduced from the forward portion of the hydraulic cylinder 9 to a pressure slightly less than the pressure set for the backward portion of the hydraulic cylinder 9.

The barrel 17 is kept under constant pressure towards the mold 6 by the pressure in the back position of the hydraulic cylinder 11. This is achieved by means of the control circuit 2 where a proportional hydraulic valve is controlled by a pressure sensor circuit $I_2$.

As the screw 8 rotates a recharge of hydrophilic polymer 4 is made from the hopper 5. During a certain time period and at a defined rotating speed of the screw 8, controlled by control circuit 3, a precise amount of polymer 4 is fed into the extruder barrel 17. Control circuit 3 is actuated by speed sensor circuit $I_3$ measuring the rotating speed of the screw 8 and sensing back to a hydraulic proportional flow control valve $O_3$ controlled by control circuit 3, thus assuring a constant rotating speed of the hydraulic motor 10, irrespective of the changing torque resulting from introduction of the polymer 4 recharge.

When the load time is completed, the screw 8 rotation is stopped and molding cycle Point D of FIG. 2 is reached. The soak time from molding cycle Points D to A of FIG. 2 allows for the polymer 14 to plasticize completely under controlled temperature conditions as controlled by control circuit 1.

A temperature sensor circuit $I_1$ senses a thyristor heat regulator $O_1$ heating the extruder barrel 17 as directed

TABLE 1

| Ranges of Time, Temperature and Pressure for the injection Molding Work Cycle of FIG. 2: | | | | | |
|---|---|---|---|---|---|
| | POINTS | | | | |
| Time (seconds) | $10^{-2}-1$ | $10^{-2}-1$ | $10^{-2}-1$ | $10^{-2}-1$ | $10^{-2}-1$ |
| Temperature (Celsius) | ambient-100 | 50-190 | 50-190 | 50-190 | 50-190 |
| Pressure $((10^5 \times N \times m^{-2})$ (Newtons per square meter) | 1-5 | 600-3000 | 600-3000 | 0-3000 | 600-3000 |

Referring now to FIG. 3 illustrating the combined injection molding device 27 and microprocessor 28 utilizing the method of present invention.

The combined injection molding device 27 and microprocessor 28 comprises six control circuits of which five are closed-loop, fully analog, and one is on-off.

by control circuit 1.

During the time interval from molding cycle Points B to E on FIG. 2, the mold 6 has cooled down sufficiently so that the finished capsule parts 7 can be ejected from the mold 6.

After ejection of the capsule parts 7, the work cycle returns to Point A of FIG. 2 where a certain volume of plasticized polymer 14 has accumulated in front of the screw 8 (sensing circuit $I_4$ is actuated and time has elapsed) so that the work cycle of FIG. 2 can be repeated.

It is important to note the temperature and humidity control loops 5 and 6, for the maintenance of precise water content of the polymer in the hopper 5, which is essential for proper operation at the desired speeds.

The microprocessor 28 includes a memory section 51 to store the desired operating parameters; a sensing and signaling section 52 to receive the sensing signals of actual operating conditions, to detect the deviation between the desired and actual operating conditions, and to send signals for adjustment through the actuating section 53 to the thyristor and valves.

Figure 4:
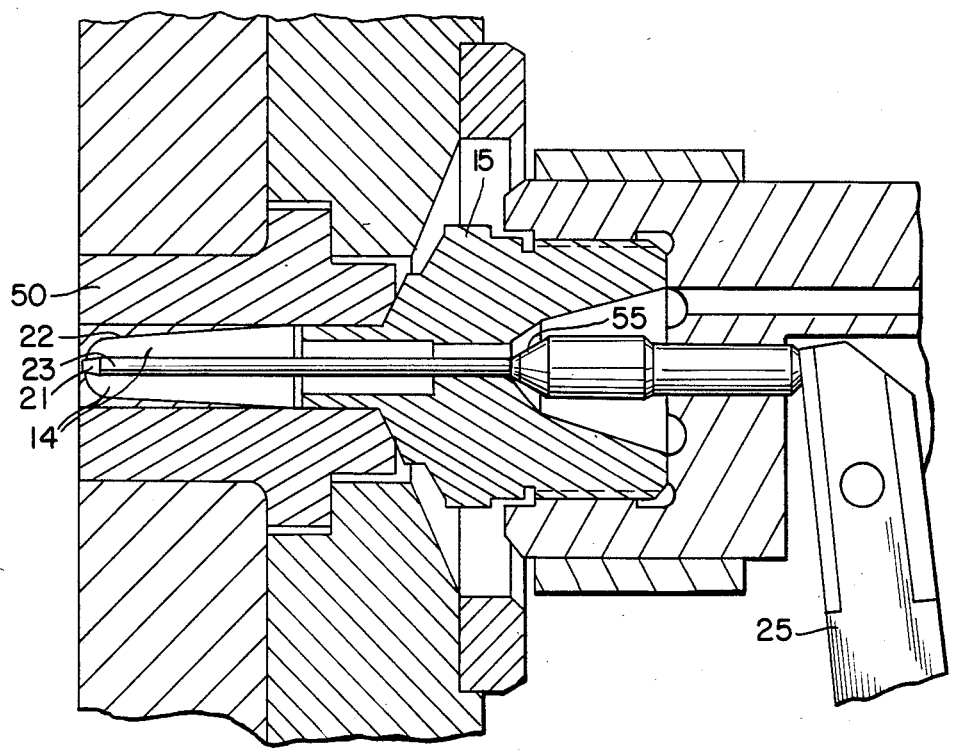
FIG. 4 is an expanded schematic of the exit end of the injection molding device.

Referring now to FIG. 4 there is shown the valve assembly 50 including the outlet port 21, the nozzle 22, the needle valve 23, and the one-way valve 15. These elements operate as follows:

At Point A in FIG. 2 the needle valve 23 is retracted for the outlet port 21 and the one-way valve 15 is retracted from the valve body 50 so as to form an inlet opening 55 for plasticized gelatin 14 into the nozzle 22 which defines a charging chamber for plasticized polymer 14. The plasticized polymer 14 is injected through nozzle 22 and into the mold 6 during the mold-filling time between Point A and B in FIG. 2. At Point C in FIG. 2 the needle valve 23 is pushed forward so as to close the outlet port 21 during which time between point C and E in FIG. 2, the mold 6 is closed and the capsule part 7 in the mold 6 is cooling. The needle valve 23 remains closed between Point E and A in FIG. 2 during which time the capsule part 7 is ejected from the mold 6. The total time period between Point B and A in FIG. 2 must be less than 5 seconds in order that the plasticized polymer 14 does not solidify in the nozzle 22. This is an important aspect of the present invention because:

a. faster production times are made possible in order to achieve greater output;

b. there is no loss of plasticized Polymer 14 in the production cycle due to solidification in the nozzle 22 and the mold 6; and c. there is a minimum risk of degradation of the plasticized polymer 14 because it remains in the production cycle for a short time and is only utilized one in each production cycle because the plasticized polymer 14 is solidified in the capsule-shaped cavities 19 and not in the nozzle 22.

The one-way valve 15 and the needle valve 23 are actuated by a spring-tensioned lever 25 which normally closes both the outlet port 21 and the nozzle 22 until the lever 25 is cam-actuated pursuant to signals from the microprocessor 28.

The thermomechanical properties of gelatin, i.e. storage and loss shear modules at different temperatures, are strongly dependent on its water content. The capsule molding process of the present invention can be used for the polymer with a water content preferably within a range of 5 to 25%. The lower limit is defined by the maximum processing temperature of 190° C. which in turn cannot be exceeded in order to avoid degradation. The upper limit is determined by the stickiness of the finished capsules. The abbreviations in Table 2 below will be used hereinafter in this application:

TABLE 2

Abbreviations of Used Physical Parameters

| ABBREVIATION | UNIT | DESCRIPTION |
| --- | --- | --- |
| $T_a, p_a$ | Degree C., $N \times m^{-2}$ | Ambient temperature and pressure. |
| H(T,P) | KJoule $\times$ Kg$^{-1}$ | Enthalpy of the hydrophilic polymer-water system at a given pressure and temperature. |
| (T,P) | $N^{-1} \times m^2$ | Compressibility of the hydrophilic polymer at a given temperature and pressure. Its numerical value is the relative volume change due to change of pressure by a unit amount. |
| (T,P) | (Degree C.)$^{-1}$ | Volumetric thermal expansion coefficient of the hydrophilic polymer at a given temperature and pressure. Its numerical value is the relative volume change due to change of temperature by a unit amount. |
| V(Q,T,P) | Kg $\times$ sec$^{-1}$ | Flow rate of the hydrophilic polymer at a given temperature and shear deformation rate and pressure. Its numerical value is |

TABLE 2-continued

Abbreviations of Used Physical Parameters

| ABBRE-VIATION | UNIT | DESCRIPTION |
|---|---|---|
| | | the volume of a melt leaving the exit crosssectional area of an injection molding device in unit time due to the deformation rate. |
| $T_{G1}; T_{G2}(X)$ | Deg C. | The temperature range of the glass-transition of the hydrophilic polymer. |
| $T_{M1;R} TM2(X)$ | Deg C. | The temperature range of the melting of the partially crystalline hydrophilic polymer. |
| $T_E(t)$ | Deg C. | The temperature of the hydrophilic polymer in the nozzle area of the injection unit. |
| $T_M(t)$ | Deg C. | The temperature of the hydrophilic polymer in the mold. |
| $P_E$ | $N \times m^{-2}$ | The pressure in the nozzle area of the hydrophilic polymer, expressed as the weight fraction of the water hydrophilic polymer system. |

For the control and regulation of the injection molding process (IMP) we need the knowledge of the
(1) heat consumption of the melting process:

$$H(T_E, P_E) - H(T_a; P_a)$$

(2) the heating rates of the hydrophilic polymers in the injection molding device. To calculate this we need the heat conduction number of the hydrophilic polymer ant the heat transfer number of the hydrophilic polymer ant the heat transfer number of the hydrophilic polymer and the specific material of construction of the barrel which is in contact with the hydrophilic polymer. The heating rate and the heat consumption of the hydrophilic polymer give the minimum time interval necessary to make the hydrophilic polymer ready to inject and the necessary heating power of the injection molding device.

(3) the $T_E$ depends on X of the hydrophilic polymers. If the water content of the hydrophilic polymer in the mold is too low the resulting $T_E$ will be too high and cause degradation. A minimum water content of 5% by weight is required to keep $T_E$ below 190° C.

(4) the flow rate V(Q,T.P) is as well strongly dependent on the water content of the hydrophilic polymer. To speed up the IMP we need a high flow rate V(Q,T,P) which can be achieved by a high water content.

The upper limit of the water content is defined by the stickiness and mechanical failure of the capsules; a water content of 25% (0.25) by weight cannot be generally exceeded. The range within which capsules can be molded by the method of the present invention if therefore within 0.05 to 0.25 of water content. Better capsules are made with a water content in the range between 0.10 and 0.20; the best capsules were made with the water content in the range between 0.12 and 0.18.

The hydrophilic polymer in the mold will reduce its volume due to the temperature change $T_M - T_a$. This would result in voids and diminution of size of the capsule, which therefor would be of unacceptable quality. It is an absolute requirement in capsule making that the dimensional absolute requirement in capsule making that the dimensional deviations are less than 1%. To compensate for shrinking by the temperature change the mold must be filled at a distance pressure $P_M$. This filling pressure is determined by the quantities (T,P) and (T,P). The injection pressure ($P_E$) depends again on $T_E$, which as was shown already is in turn strongly dependent on X.

Figure 5:
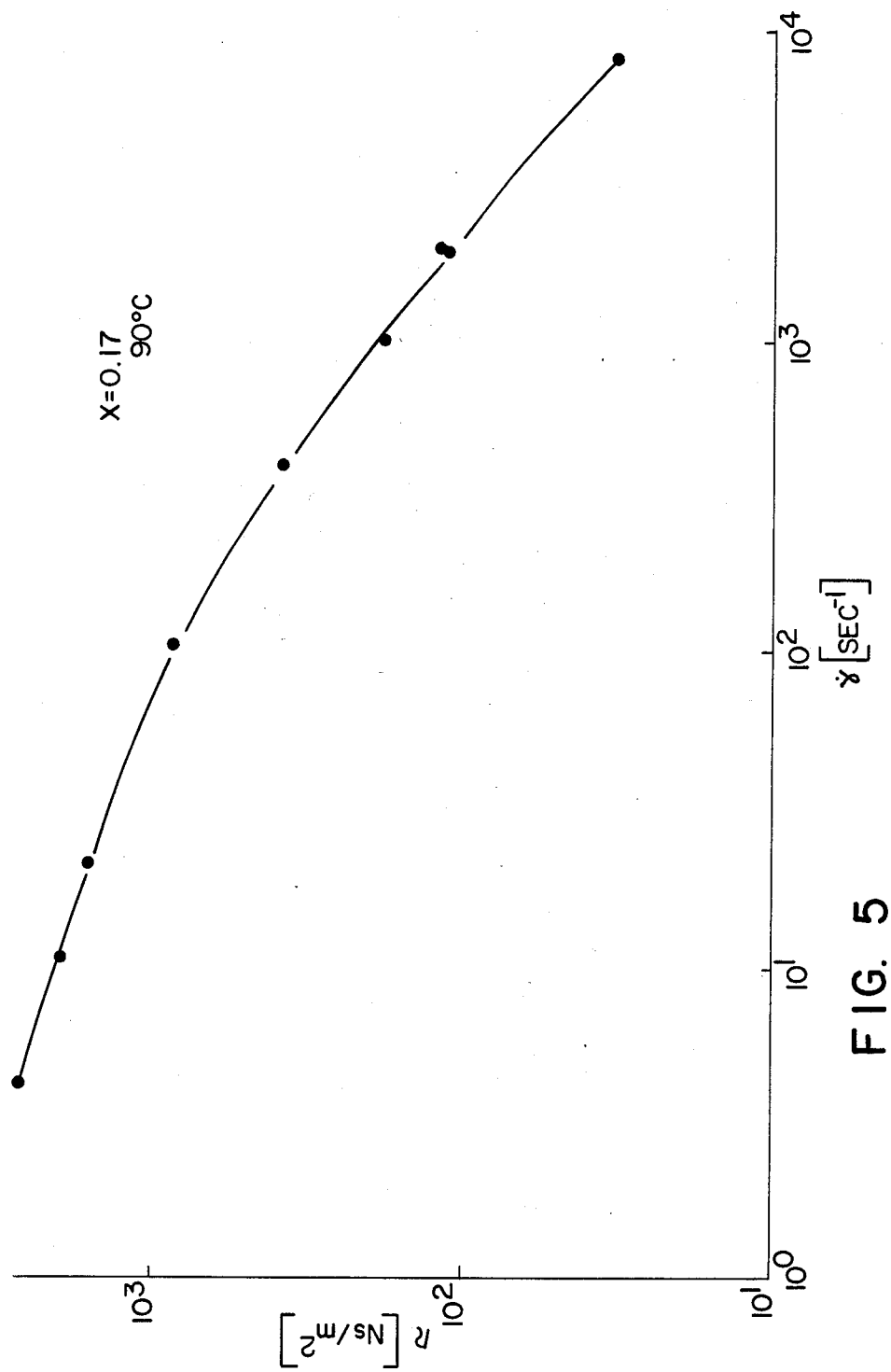
FIG. 5 is the diagram of dependence of shear viscosity of gelatin within the pertinent ranges of the shear rate in the present invention.

Referring now to FIG. 5, the shear rate dependent shear viscosity of gelatin at 90° C. is show for gelatin with a water content X of 0.17. The capillary has a diameter of d=1.05 mm, and a length of 5.0 mm; the ration of length to diameter is therefor L/d=4.75.

Figure 6:
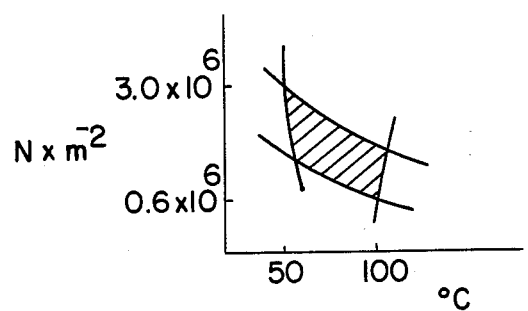
FIG. 6 is the diagram of molding area for gelatin within the ranges of time, temperature, pressure and water content of the hydrophilic polymer for the present invention.

Referring now to FIG. 6, the molding are diagram for gelatin with water content of 0.17. During injection molding the plasticized gelatin is discontinuously extruded and immediately cooled in a mold of the desired shape of the capsule part. Moldability depends on the polymer properties and the process conditions, of which the thermomechanical properties of the gelatin as well as the geometry and the temperature and pressure conditions of the mold are the most important. In the molding area diagram of FIG. 6 the limits of pressure and temperature are indicated for the processing of gelatin in the combined injection molder-microprocessor of the present invention. The maximum temperature of 190° C. is determined by visible degradation of the polymer above that limit. The lower temperature limit of 50° C. was determined by the development of too high viscosity and melt elasticity in the recommended water content range X: 0.05 to 0.25. The higher pressure limits of $3 \times 10^8 \times m^{-2}$ are given by the start of flashing when the melted polymer flows in a gap between the various metal dies which make up the molds, thus creating thin webs attached to the molded capsule parts at the separating lines. The lower pressure limits of about $6 \times 10^7 N \times m^{-2}$ are determined by short shots, when the mold cannot be completely filled by the polymer.

| WORKING PARAMETERS FOR INJECTION MOLDING PROCESS | |
|---|---|
| Density | $1.3–1.2 \times 10^3$ kg $\times$ m$^{-3}$ |
| Crystallinity | 25% |
| $H(T_E,P_E) - H(T_a,P_a)$ | 0.32 KJoule $\times$ kg$^{-1}$ |
| Net heating performance for 10 kgs. melt/h (corresponding to $10^6$ capsules/h) | $3.5 \times 10^5$ KJoule |
| Heat conduction number (20° C.) for gelatin | 1.0 KJoule $\times$ m$^{-1}$ $\times$ h$^{-1}$ $\times$ Degree$^{-1}$ |
| Compressibility $(T_E,P_E)$ | $5 \times 10^{-10}$ N$^{-1}$ $\times$ m$^2$ |
| $(T_a, P_a)$ | $8 \times 10^{-5}$ (Degree C.)$^{-1}$ |
| Contraction due to crystallization | negligible |
| Critical shear deformation rate | $10^4–10^5$ sec$^{-1}$ |

Figure 7:
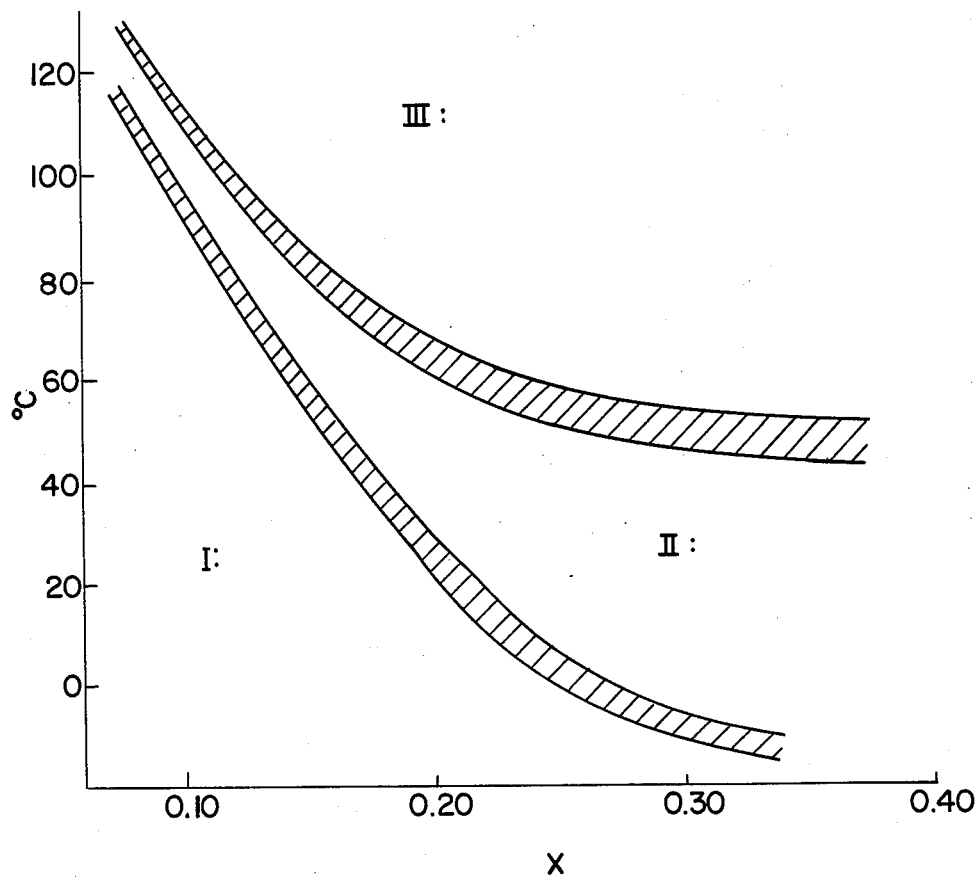
FIG. 7 is the diagram of dependence of glass transition temperature range and melting temperature range for the pertinent water content ranges of gelatin a representative hydrophilic polymer, the subject of U.S. Ser. No. 698,264 the parent of this application.

The hydrophilic polymers are extruded and injected under the following conditions:

Referring now to FIG. 7 the glass transition range and the melting temperature range as a function of the composition of the polymer-water system is shown. Gelatin is representative of similar polymer systems within this invention although specifically excluded because it is the subject of the parent application. At temperatures below the glass transition range ordinary gelatin, as available commercially, is a partially crystalline hydrophilic polymer containing approximately 70% amorphous and approximately 30% crystalline parts by volume (Area I in FIG. 7). Such gelatin preparations are commonly called cold dryed gelatins. By raising the temperature of said gelatin preparation at a distinct water content the gelatin passes through the glass transition range.

Referring to FIG. 1 said heating process of the polymer will take place within the extruder barrel 17. Referring to FIG. 2 said heating process of the polymer will take place during the entire injection molding work cycle. The area in FIG. 7 between the glass transition range and the melting polymer and a polymer melt. The glass-transition is not thermodynamic transition range of any order but is characterized by a change of the molecular movement of the polymer molecules and by a change of the bulk storage module of the amorphous gelatin by several orders of magnitude. By passing from area II to are I in FIG. 7 the translational movements of the molecules or those of large parts of said molecules will be frozen in the glass transition temperature range and this is reflected by a change in the specific heat ($C_p$) and the volumetric thermal expansion coefficient (a) in said temperature range. By passing from area II to area III due to crossing the melting range of the crystalline gelatin the helically ordered part of the gelatin will melt.

Figure 8:
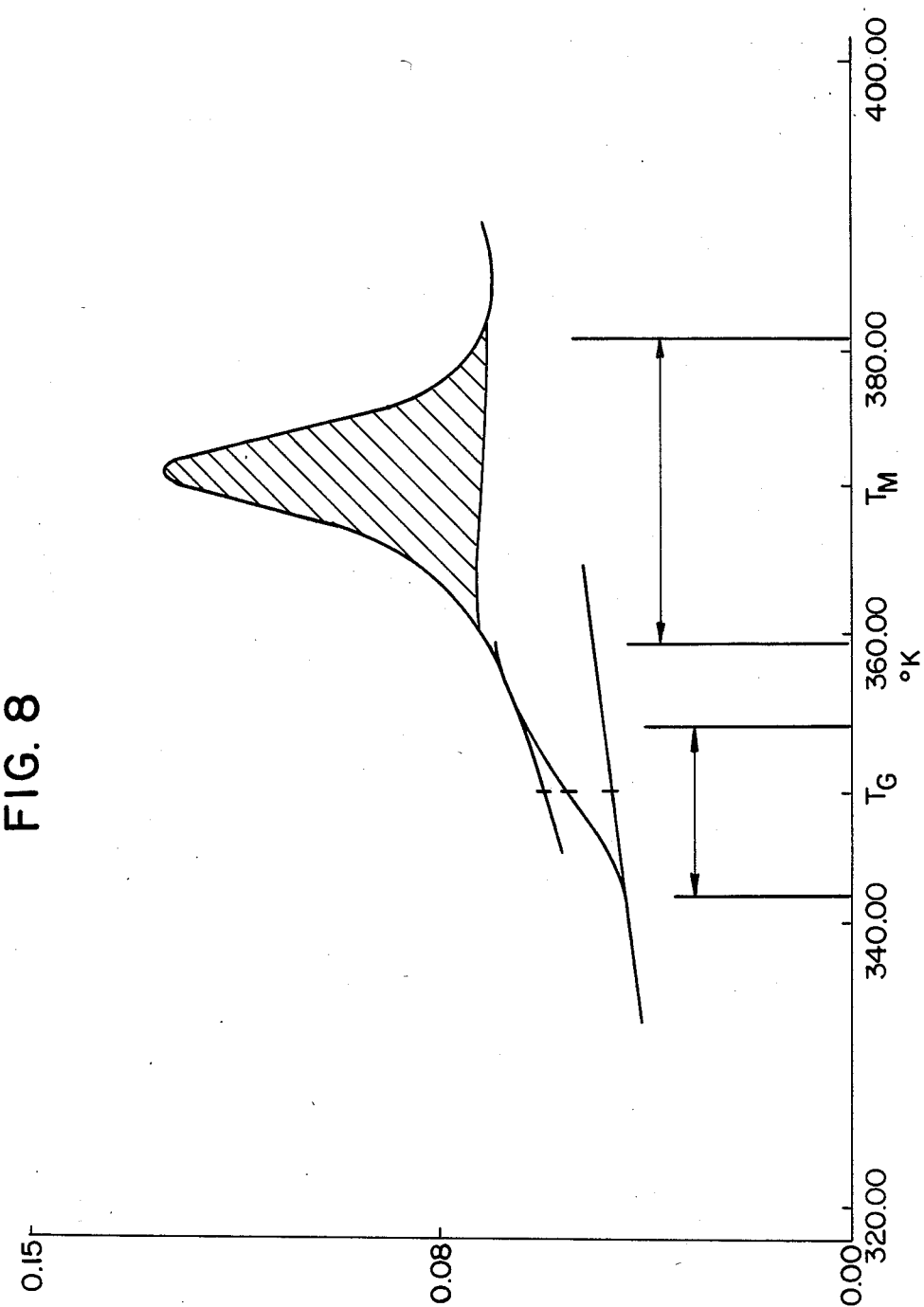
FIG. 8 is the diagram of dependent of differential calorimeter scan in which the heat consumption rate of the polymer covered by U.S. Ser. No. 698,264 application now U.S. Pat. No. 4,655,840 gelatin is plotted for the pertinent temperature range of the present invention these values being representative of all hydrophilic polymers.
Figure 9:
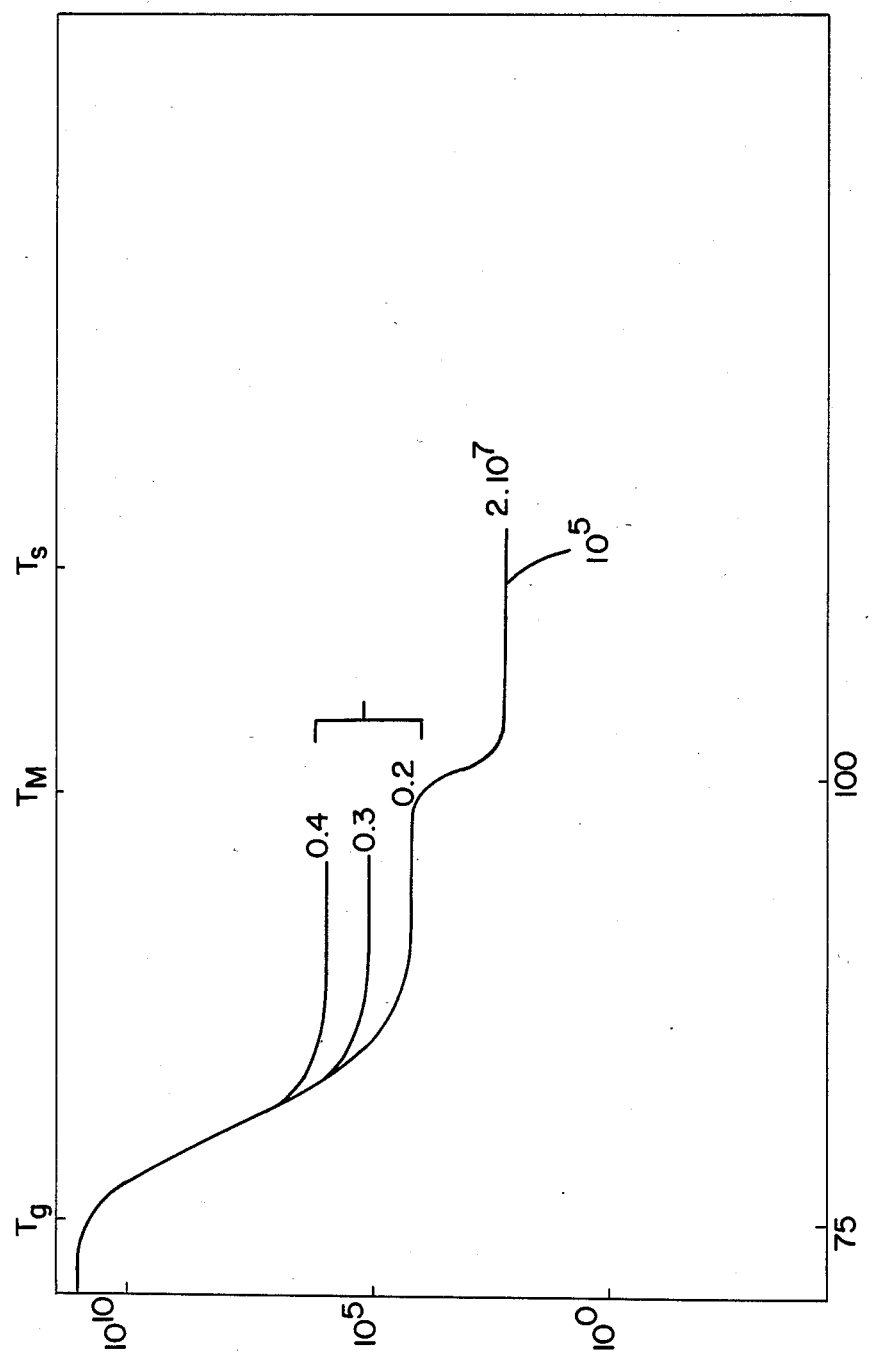
FIG. 9 is a diagram of the logarithmic bulk elastic storage module of the gelatin as representative of the temperature range of the present invention.

The heating process of the gelatin or similar polymer will take place within the extruder barrel 17. Referring to FIG. 2 the heating process of the polymer will take place during the entire injection molding work cycle. Said helix-coil transition is a true thermodynamic transition of the first order and is an endothermic process. These transitions can be detected by scanning calorimeter or by measurement of the change of the linear viscoelastic bulk storage module due to change of the temperature. A typical plot of temperature scan with a differential calorimeter is shown in FIG. 8. On the ordinate is plotted the velocity of the heat consumed by the sample relative to a reference (empty sample holder). The velocity of heat consumption of the sample is due to the change of the temperature of the sample, and said temperature is plotted on the abscissa as degrees Kelvin. The base line shift on said plot is corresponding to the glass transition and the peak to the melting or to the helix-coil transition. The linear viscoelastic bulk storage module E can be measured at small sinusoidal shear deformations of the polymer sample. The change of said module of a typical gelatin sample at water content $X=0.13$ is plotted as a function of the sample temperature in FIG. 9. This value is similar to the hydrophilic polymers of this invention having both crystalline and amorphous structure at the glass transition temperature and at the melting or helix-coil transition temperature said module changes several orders of magnitude. As is shown in FIG. 9 there exist a further transition temperature above the melting range, and said transition is characterized by a further drop in said module e. We will call the temperature of said transition the solution temperature. In the temperature rant $T_g$ to $T_M$ the gelatin is in the rubber elastic state, and the crystalline ranges or fibrils represent the elastically active elements of the network.

Similar networks exist for example in the plasticized microcrystalline polyvinylchloride (PVC). The crystalline regions give rise to diffraction patterns of x-rays in said PVC but not in the gelatin [I. Tomka, Chimia 30, 534–540 (1976); I. Tomka et al. Phot. Sci. 23, 97 (1975)]. In the temperature rant $T_M$ to $T_S$ the gelatin is in the viscoelastic rubber-elastic state. The elastically active network in said state of the gelatin is like in most polymer melts a temporary network. Said temporary network is due to entanglements of the polymer molecules. Specifically in the gelatin the strong interactions between the macromolecules (hydrogen-bridges, dipol-dipol interactions) contribute an important part to the elastically active temporary network. At the solution temperature said temporary network disrupts and the gelatin molecules, specifically due to the presence of water, dissolve. At a temperature higher than $T_S$ the storage module drops to extremely low values: less than $10 \times Nm^{-2}$, as shown in FIG. 9. In the present invention it was found that the processing (injection molding, blow molding etc.) of the polymer should proceed at a temperature height than $T_S$.

Referring to FIG. 1 the heating of the gelatin or similar polymer to a temperature height than $T_S$ takes place in the forward part of the extruder barrel 17. Said heating process will be maintained not only by the steam heating coils 18 but to an important proportion by the internal friction during the injection process due to the high deformational rates. Referring to FIG. 2 said dissolution process will take place especially between point A and B of the work cycle. It was found that the reversible elastic deformation of the injection molded polymer after opening the mold 6 is negligible if the temperature of the gelatin during the injection process is high than $T_S$, otherwise the molding sequence would drop by at least an order of magnitude.

Referring to FIG. 2 the necessary cooling period for the polymer in the molds—to prevent any reversible elastic deformation of said polymer—will take place between points B and E of the working cycle. A restriction of the molding sequence to low speed coupled with long keeping of the gelatin in the mold (larger than 5 sec) is undesirable because of two reasons: low output of the product and loss of water content of the gelatin in the extruder. At the elevation injection temperature there is always a transport of water from the hot to the cold polymer in the extruder barrel. (See D. Gehrmann, Thesis, University of Darmstadt 1979). Said water transport can be compensated due to the transport of the polymer by the screw in the opposite direction.

Figure 11:
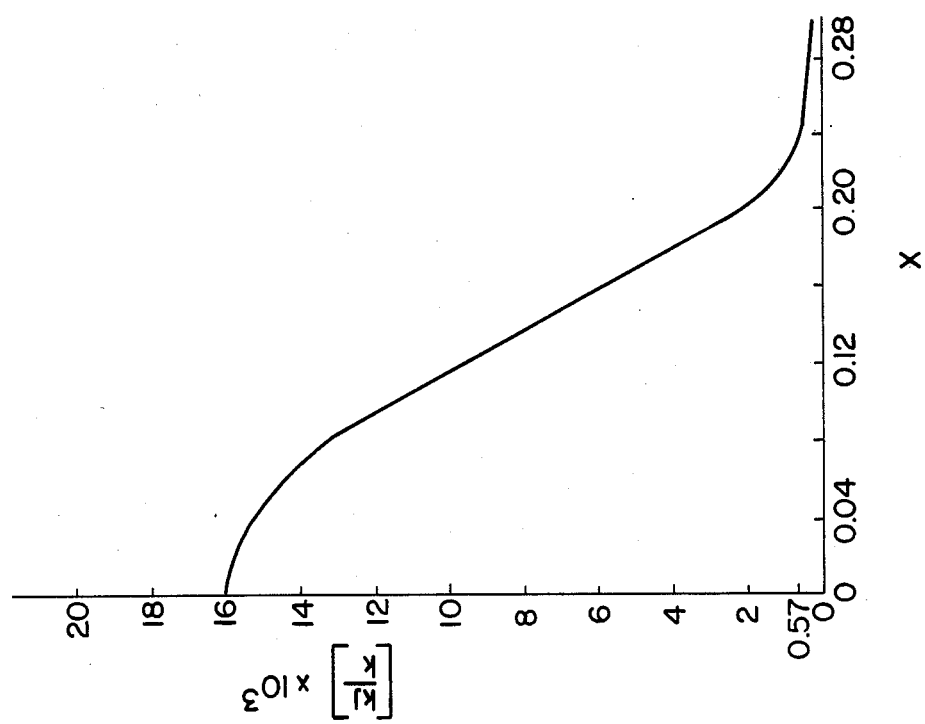
FIG. 11 is a diagram of dependence of differential heat of water adsorption in the pertinent range of water content of the gelatin which is representative of the polymers of the present invention.
Figure 10:
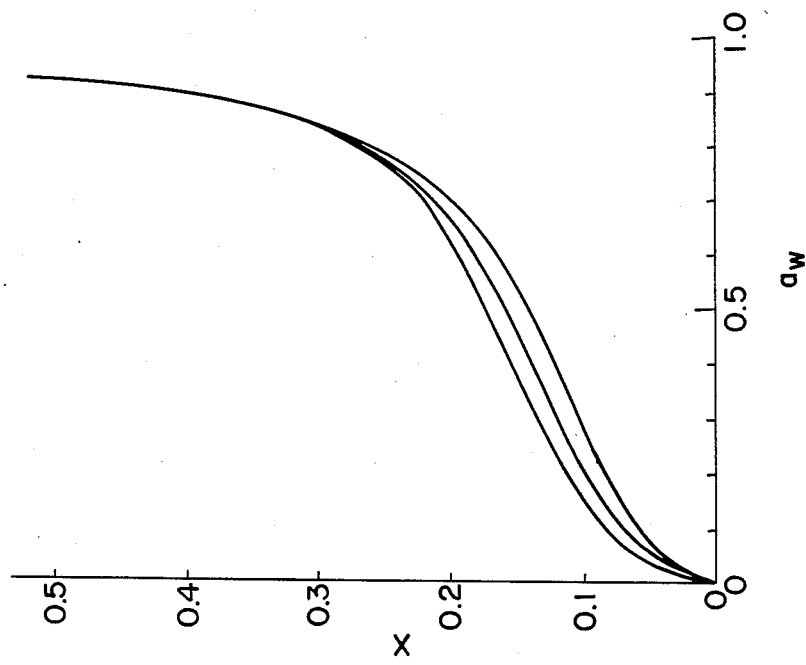
FIG. 10 is a diagram of dependence of equilibrium water content of the gelatin in the entire water activity range with is representative of the hydrophilic polymers of the present invention.

Referring to FIG. 1 said transport of polymer will be maintained by screw 8. Referring to FIG. 2 said transport of gelatin will take place between the points A and B and further between the points C and D of the working cycle. To build up a stationary water content of the polymer in the melting area of the extruder barrel it is necessary to work at an injection sequence which is shorter than 5 sec. To establish a constant and high enough water content of the hydrophilic polymer in the extruder barrel it is further necessary to use hydrophilic polymers with the proper shape of both the sorption isotherm (see FIG. 10) and the differential heat of sorption as a function of the water content (see FIG. 11). The constant water content of the hydrophilic polymer in the extruder barrel is necessary due to the maintenance of constant production conditions. The water content of the hydrophilic polymer during the injection must fulfill the conditon: X high than 0.05 otherwise $T_S$ is also high than 190° C. and this is undesirable due to degradation of the polymer. The condition which is necessary to avoid is a phase separation of the polymer in-water phase into the two liquid phases of polymer water and water. This phase separation could result in the extruder barrel during injection and is avoided by having water activity ($a_{W,M}$) of the polymer (at the highest temperature in the extruder barrel and for the water content range of 0.05 to 0.25 of the hydrophilic polymer) less than one.

By the present invention we could drop the processing temperature of a hydrophilic polymer by at least 100° C. which means we could shift the processing temperature ($T_p$) by incorporating sufficient water (X is more than 0.05 and less than 0.25) during processing of said hydrophilic polymer leading to a range of the temperature 50° to 190° C. where no degradation of said hydrophilic polymer during the processing takes place. The melting range of typical aliphatic polyamides with water content less than 0.002 is between 200° and 250° C. Polyamides for example show the following behavior with respect to their compatibility with water during processing. The sorption isotherm of nylon 6 for example has no inflection point, its differential heat of sorption is not a monotonously decreasing function with the water content and already at room temperature the sorption isotherm shows an equilibrium water activity value equal to a water content for 0.05. If we now incorporate about 0.035 water content in said polyamide at ambient temperature we will find already a phase separation of water and water-polyamide phases below 100° C. Because the nylon 6 polymer is not molten at the said water content and at temperatures below 100° C. the said polymide is not processable. At a water content of 0.035 and temperatures equal to or higher than 100° C. the said polyamide is again not processable due to the syneresis of water in the extruder and the mold. This effect is well known in the corresponding literature (Kunstoff Handbuch, Volume 6: Polyamide, Editors: R. Viewegen, A. Muller, Karl Hanser Verlag, Munich, w. Germany 1966).

In the procedure of branching and crosslinking of hydrophilic polymers, it is important to add the crosslinking agents, especially the covalent crosslinking agents, shortly before injection of the molten hydrophilic polymers.

Referring now to FIG. 9 of the present invention it can be concluded that an increase of the molecular weight of said hydrophilic polymers would raise the solution temperature of the said polymers.

Due to possible degradation at elevated processing temperature it is not desirable to branch or crosslink said hydrophilic polymers before injection.

Referring to FIG. 1, an aqueous solution of crosslinking agents is injected in front of a mixing system being placed between the melting and plasticizing unit 4 and the injection unit 1. The crosslinking reaction mainly occurs during the injection cycle and the time after ejection of the capsule. By the above described technology on branching and crosslinking there is no disadvantage of changing the thermomechanical properties of the hydrophilic polymers during the melting and solution process.

The hydrophilic polymers preferably various types of gelatin are extruded and injected under the following condition given in Table 3 below:

TABLE 3

| Injection Conditions for Hydrophilic Polymers | | | | |
|---|---|---|---|---|
| Injection Unit | | | | |
| Screw diameter | mm | 24 | 28 | 32 |
| Injection pressure | $N \times m^{-2}$ | $2.2 \times 10^8$ | $1.6 \times 10^8$ | $1.2 \times 10^8$ |
| Calculated swept volume | $cm^3$ | 38 | 51.7 | 67.5 |
| Effective screw length | L:D | 18.8 | 16.1 | 13.5 |
| Plasticizing capacity (PS) | kg/h (max.) | (1a)13.5 (11a) 9.2 (1b)23.6 (11b)17.5 | 21.2 14.5 34 27 | 21.5 15 36 27.5 |
| Screw stroke | mm (max.) | 84 | 84 | 84 |
| Injection capacity | kW | 30 | 30 | 30 |
| Injection velocity | mm/s (max.) | 460 | 460 | 460 |
| Nozzle contact force | kN | 41.2 | 41.2 | 41.2 |
| Screw rotating speed | $min^{-1}$ | Var. (1a) 20 (11a) 20 Var. (1b) 20 (11b) 20 | | −280 −170 −600 −400 |
| Number of heading zones | | 5 | 5 | 5 |
| Installed heating capacity | kW | 6.1 | 6.1 | 6.1 |
| Molding unit | | | | |
| Clamping force | kN | | | 600 |
| Opening stroke | mm | | 100 | −250 |

In addition to the present invention for molding capsules, one skilled in the art could also use this disclosure to produce capsules utilizing profile extrusion, compression molding, vacuum forming, thermal forming, extrusion molding polymer casing in combination with vacuum forming.

While the preferred embodiment of the injection molding-microprocessor apparatus is for the method of producing capsules from various hydrophilic polymer types, it had been found that quality capsules may also be manufactured utilizing the present invention by adding just before injection covalent and/or non-covalent crosslinking agents such as: multivalent metal salts such as aluminum and calcium salts, boric acid, potassium alum, ammonium alum and the like; metal salts of chromium, aluminum or zirconium (chromium acetate, chromium alum) as described in patent Nos. DT 24 39 553 A1, DT 26 26 026 A1, DT 21 48 428, and DT 25 05 746; aldehydes and ketones as well as their halogenated derivatives as formaldehyde, paraformaldehyde, 2, 4, 6, trinitro-benzaldehyde, quinones (benzoquinone), 1,2 and 1,3 dicarbonyl compounds such as glyoal, cyclohexandion-1,2; 1,5 dialdehydes (glutaraldehyde); acids and acid anhydrides such as mucochloric acid, chorides of 2-basic organic acids, anhydrides of tetracarboxylic acids; compounds with more than 2 easy-breaking hetrocyclic 3-membered rings as ethylene oxide and ethylenimine; polyfunctional methene-sulfonic acid ester; non nitrogen polyfunctional compounds including ethylene glycoldimethacrylate, diepoxy butane, epichlorohydrin, dichloropropanol, diethylene glycoldimethacrylate, dichloromethyl and dichlorooctyl ethers and the like; nitrogen containing polyfunctional compounds as e.g. hexamethylene diisocyanate, dimethyl adepimate, bisdiazobenzidine, Woodward's reagent K, N,N$^1$-(1,3-phenylene) bismaleimide, N,N$^1$-ethylene-bis-(iodoacetamide), urea, trichloro isocyanuric acid, ethylene-bismethacrylamide, tetrachloropyrimidine, dimethylol urea, dimethylol ethylene urea, methylol and dimethylol acrylamide as well as the following group of crosslinking agents described in the patent Nos. De 23 48 294 B2, DT 24 39 553 A1, DT 25 05 746 A1, DT 26 25 026 A1, EUR 0,021,018, U.S. Pat. No. 3,321,313, and DT No. 21 48 428;
carbodiimides;
sulfobetain cabodiimides;
carbamoyl oxypyridinium salts;
carbamoylonium salts;
1-N-ethoxy-carboxy-2-ethoxy-dihydrochinoline;
isoxazolium salts;
bis-isorsyolium salts; and
diisocyanates.

For the manufacturing of capsules with the above described hydrophilic polymers the utilization of plasticizers, lubricants and coloring agents specifically of pharmaceutical grades leads to optimal product qualities.

Pharmacologically acceptable plasticizers, such as polyethylene glycol or preferably low-molecular weight organic plasticizers, like glycerol, sorbitol, dioctyl-sodium sulfosuccinate, triethyl citrate, tributyl citrate, 1,2 propylenglycol mono-, di- tri-acetates of glycerol etc. are utilized at various concentrations of about 0.5–40% preferably at 0.5–10% based upon the weight of the hydrophilic polymer.

Pharmacologically acceptable lubricants, such as the stearates of aluminum, calcium, magnesium and tin; as will as talc, silicones, etc. are to be used at contractions of about 0.1–10% preferably at 0.1–5% based upon the weight of the hydrophilic polymer.

Pharmaceutically acceptable coloring agents, such as azo-dyes and other dyestuffs and pigments as iron oxides titanium dioxides, natural dyes etc. are used at concentrations of about 0.001–10% preferably at 0.001–5% based upon the weight of the hydrophilic polymer.

For the manufacturing of capsules with the above described polymers the utilization of plasticizers, lubricants and coloring agents preferably of pharmaceutical grades leads to optimal product qualities.

In addition it has been found that quality capsules can be made with the injection molding-microprocessor apparatus utilizing the method of the present invention with other polymers having enteric properties (2 hours resistant in gastric juice, soluble within good 30 min in intestinal juice according to USP XX) as: hydroxypropyl methylcellulosephthalate (HPMCP), polyvinyleacetatephthalate (PVAP), celluloseacetylphthalate (CAP), acrylates and methacrylates (eudragit), phthalated gelatin, succinated gelatin, crotonic acid, and shellac. Said polymers having enteric properties may be combined with various extenders of such as various grades of gelatin and/or gelatin modified by covalent and non-covalent crosslinking agents or combinations of more than one covalent and non-covalent crosslinking agents, vegetable proteins as sunflower proteins, soybean proteins, cotton seed proteins, peanut proteins, rape seed proteins, blood proteins, egg proteins, and acetylated derivatives thereof and the like, alginates (linear multiblock copolymers of blocks of B-(1,4)-D-mannuronic acid and a- (1,4)-L-gluronic acid as well as alternating copolymers of both these principal constitutents), lactose, gum arabic, cellulose and water soluble derivatives of cellulose such as hydroxyethylcellulose hydroxypropylcellulose, hydroxypropylmethylcellulose, hyroxymethylcellulose, water soluble acrylic acid polymer, vinyl acetate polymer, polyvinylpyrrolidone, and water soluble polysaccharides, like agar-agar.

Examples of capsule manufacture with some of the useful hydrophilic polymers of this invention follow. One of the polymer, HPMCP, is chosen as as exemplary for use with several additives discussed above. Suitable representatives from this additive class can be combined with the other hydrophilic polymers set forth above.

The following ingredients are used in various examples and are identified as indicated below.

The microfine cellulose used was ELCEMA G250 by Degussa, Frankfurt and SOLKA FLOC Five granular, lot 1-4-20x. Other types and brands of microfine cellulose could be used such as ELCEMA P050, P100, or F150, also obtainable from Degussa.

The cellulose acetate phthalate used contained 30–40% phthalate groups, 17–23% acetate groups, and about 6% free acid groups. A suitable commercial product for use in these examples is obtained from Eastman Kodak Col, Rochester, N.Y.

Polyethyleneglycol of molecular weight of 10,000 was used. However other PEG's can be used, preferably with a molecular weight greater than 1,000. Commercial brands of PEG suitable for use in these examples include but are not limited to: CARBOWAX by Union Carbide, NY, PLUROCOL by Wandotte, Michigan, POLYGYCOL by dow chemical, Michigan, POLYGLYKOL E by Hoechst, Franfut, POLY-WACHS by Huls, Marl, TETRONIC by Kuhlman, Paris and LANOGEN by Hoechst, Frankfurt.

The HPMCP used had a molecular weight of 20,000. A suitable commercial brand for use in these examples is HPMCP HP 50 obtained from Shinetsu Chemical Co., Tokyo.

The soy protein used was of normal food grade and is obtainable as PURINA PROTEINS from Ralston Purina, Missouri.

The HPMC used contained 19–30% methoxy, 3–12% hydroxypropyl groups and had a molecular weight of 6000. It is obtainable as VISCONTRAN from Henkel, Dusseldorf.

The Na-CMC used had an average molecular weight of 250,000 with a degree of substitution of 0.7. It was obtained as HERCULES CMS from Hercules Powder Co., Delaware.

The PVP used had a pH of 3.5–5.0 in a 1% solution and had an average molecular weight of 10,000. It is obtainable a KOLLIDON from BASF AG, Ludwigshafen.

The macromolecule probably consists of the alternating copolymers B-D-galactopyranosyl-and 3,6-Anhydro-a-L-galactopyranosyl-residue linked in the (1,3) position. The agar-agar used is of normal food grade, 60–80 mesh size.

The principal chain of the gum arabic polysaccaride consists essential of 1,3 D-galactopyranose units. The gum arabic used had an average molecular weight of between 200,000 and 300,000.

The methyl cellulose used had a degree of substitution of approximately 2. It is obtained as VISCONTRAN MC 400 from Henkel, Dusseldorf.

While there have now been described and illustrated several embodiments of the present invention, the scope and working range of the present invention shall not be limited by the examples given above. The invention comprises as well various changes and modifications which will occur to those skilled in the art.

It is intended in the appended claims to cover all such changes and modifications as fall within the true spirit and scope of the present invention.

EXAMPLE 1

A batch of HPMCP with a certain content of water (and glycerin, polyethyleneglycol and calcium-stearate) was prepared and conditioned and then tested in an injection molding machine. A batch of HPMCP in powdered form was conditioned as follows:

The HPMCP of which the water content was 2% and the other additives were filled into a drum and sprayed with a specially fine spray of water to the calculated content as specially fine spray of water to the calculated content as wanted. The batch was then thoroughly mixed and stored in a closed drum for half a day at ambient temperature. Acceptable capsules were then produced according to the working conditions listed on Table 1 below:

TABLE 1

| Material Composition: | HPMCP: 89%; glycerin: 6.4%; PE-glycol (10.000): 1.6%; Ca—stearate: 3% | | | | |
|---|---|---|---|---|---|
| $T_b$ | $T_m$ | $T_e$ | $T_g$ | L/D | LFV |
| 125 | 135 | 140 | 140 | 66 | 820 |

The 6.4% by weight of glycerin were added as a softener. The 1.6% by weight of polyethylenglycol were added as plasticizer.

The 3% by weight of calcium-stearate were added as a lubricants.

The resulting capsules have enteric properties (2 hours resistance in gastric juice, soluble within well 30 minutes of intestinal juice according to USP XX).

EXAMPLE 2

A batch of HPMCP with ascertain content of water (and glycerin, polyethlenglycol, calcium-stearate and microfine cellulose) was prepared and conditioned and then tested in an injection molding machine. A batch of HPMCP in powdered form was conditioned as follows:

The HPMCP of which the water content was 2% and the other additive were filled into a drum and sprayed with a specially fine spray of water to the calculated content as wanted. The batch was then thoroughly mixed and stored in the closed drum for half a day at ambient temperature. Acceptable gelatin-like capsules were then produced according to the working conditions listed on Table 2 below:

TABLE 2

| Material Composition: | HPMCP: 57.4%; glycerin: 4.1%; PE-glycol (10.000): 1%; Ca—stearate: 2%; microfine cellulose: 27.6%; water: 7.9% | | | | |
|---|---|---|---|---|---|
| $T_b$ | $T_m$ | $T_e$ | $T_g$ | L/D | LFV |
| 110 | 120 | 140 | 140 | 66 | 835 |

The 4.1% by weight of glycerin were added as a softener. The 1% by weight of polyethylenglycol was added as a plasticizer. The 28% by weight of calcium-stearate were added as a lubricant.

The 27.6% by weight of microfine cellulose were added as an extender.

The resulting capsules have enteric properties (2 hours resistance in gastric juice, soluble within well 30 minutes in intestinal juice according to USP XX).

EXAMPLE 3

A batch of HPMCP with a certain content of water (and glycerin, polyethlenglycol, calcium-stearate and microfine cellulose) was prepared and conditioned and then tested in an injection molding machine. A batch HPMCP in powdered form was conditioned as follows:

The HPMCP of which the water content was 2% and the other additives were filled into a drum and sprayed with a specially fine spray of water to the calculated content as wanted. The batch was then thoroughly mixed and stored in the closed drum for half a day at ambient temperature. Acceptable gelatin capsules were then produced according to the working conditions listed on Table 3 below:

TABLE 3

| material Composition: | HPMCP: 74.9%; glycerin: 5.4%; pe-GLYCOL (10.000): 1.3%; Ca—stearate: 2.5%; microfine cellulose: 9.4%; water: 6.5% | | | | |
|---|---|---|---|---|---|
| $T_b$ | $T_m$ | $T_e$ | $T_g$ | L/D | LFV |
| 110 | 120 | 140 | 140 | 66 | 880 |

The 5.4% by weight of glycerin were added as a softener. The 1.3% by weight of polyethylenglycol were added as a plasticizer.

The 2.5% by weight of calcium-stearate were added as a lubricant.

The 9.4% by weight of microfine cellulose were added as an extender.

The resulting capsules have enteric properties (2 hours resistance in gastric juice, soluble within well 30 minutes in intestinal juice according to USP XX)

EXAMPLE 4

A batch of HPMCP with a certain content of water (and glycerin, polyethylenglycol, calcium-stearate and Na-CMC) was prepared and conditioned and then tested in an injection molding machine. A batch of HPMCP in powdered form was conditioned as follows:

The HPMCP of which the water content was 2% and the other additives were filled into a drum and sprayed with a specially fine spray of water to the calculated content as wanted. The batch was then thoroughly mixed and stored in the closed drum for half a day at ambient temperature. Acceptable gelatin like capsules were then produced according to the working conditions listed on Table 4 below:

| Material Composition: | HPMCP: 74.7%; glycerin: 5.4%; PE-glycol (10.000): 1.3%; Ca—stearate: 2.5%: Na—CMC: 9.4%; water: 6.7% | | | | |
|---|---|---|---|---|---|
| $T_b$ | $T_m$ | $T_e$ | $T_g$ | L/D | LFV |
| 110 | 120 | 140 | 140 | 66 | 850 |

The 5.4% by weight of glycerin were added as a softener. The 1.3% by weight of polyethylenglycol were added as a plasticizer.

The 2.5% by weight of calcium-stearate were added as a lubricant.

The 9.4% by weight of Na-CMC were added as an extender. The resulting capsules have enteric properties (2 hours resistance in gastric juice, soluble within well 30 minutes in intestinal juice according to USP XX).

EXAMPLE 5

A batch of HPMCP with a certain content of water (and glycerin, polyethlenglycol, calcium-stearate and agar) was prepared and conditioned and then tested in an injection molding machine. A batch of HPMCP in powdered form was conditioned as follows:

The HPMCP of which the water content was 2% and the other additives were filled into a drum and sprayed with a specially fine spray of water to the calculated content as wanted. The batch was then thoroughly mixed and stored in the closed drum for half a day at ambient temperature. Acceptable capsules were then produced according to the working conditions listed on Table 5 below:

TABLE 5

| Material Composition: | HPMCP: 37.4%; glycerin: 2.7%; PE-glycol (10.000): 0.7%; Ca—stearate: 1.3%; agar: 42%; water: 15.9% | | | | |
|---|---|---|---|---|---|
| $T_b$ | $T_m$ | $T_e$ | $T_g$ | L/D | LFV |
| 110 | 120 | 130 | 130 | 66 | 830 |

The 2.7% by weight of glycerin were added as a softener. The 0.7% by weight of polyethylenglycol were added as a plasticizer.

The 1.3% by weight of calcium-stearate were added as a lubricant.

The 42% by weight of agar were added as an extender.

The 9.4% by weight of Na-CMC were added as an extender. The resulting capsules have enteric properties (2 hours resistance in gastric juice, soluble within well 30 minutes in intestinal juice according to USP XX)

EXAMPLE 6

A batch HPMCP with a certain content of water (and glycerin, polyethlenglycol, calcium-stearate and agar) was prepared and conditioned and then tested in an injection molding machine. A batch of HPMCP in powdered form was conditioned as follows: The HPMCP of which the water content was 2% and the other additives were filled into a drum and sprayed with a specially fine spray of water to the calculated content as wanted. The batch was then thoroughly mixed and stored in the closed drum for half a day at ambient temperature. Acceptable gelatin capsules were then produced according to the working conditions listed on Table 6 below:

TABLE 6

| Material Composition: | HPMCP: 69%; glycerin: 5%; PE-glycol (10.000): 0.7%; Ca—stearate: 2.3%; agar: 8.7%; water: 13.8% | | | | |
|---|---|---|---|---|---|
| $T_b$ | $T_m$ | $T_e$ | $T_g$ | L/D | LFV |
| 110 | 125 | 135 | 135 | 66 | 830 |

The 5% by weight of glycerin were added as a softener. The 1.2% by weight of polyethylenglycol were added as a plasticizer.

The 2.3% by weight of calcium-stearate were added as a lubricant.

The 8.7% by weight of agar were added as an extender. The resulting capsules have enteric properties (2 hours resistance in gastric juice, soluble within well 30 in intestinal juice according to USP XX).

EXAMPLE 7

A batch of HPMCP with a certain content of water (and glycerin, polyethlenglycol, calcium-stearate and hydroxypropylmethylcellulose) was prepared and conditioned and then tested in an injection molding machine. A batch of HPMCP of which the water content was 2% and the other additives were filled into a drum and sprayed with a specially fine spray of water to the calculated content as wanted. The batch was then thoroughly mixed and stored in the closed drum for half a day at ambient temperature. Acceptable capsules were then produced according to the working conditions listed on Table 7 below:

TABLE 7

| Material Composition: | HPMCP: 39.9%; glycerin: 2.9%; PE-glycol (10.000): 0.7%; Ca—stearate: 1.3%; HPMC: 44.9%; water: 10.3% | | | | |
|---|---|---|---|---|---|
| $T_b$ | $T_m$ | $T_e$ | $T_g$ | L/D | LFV |
| 110 | 120 | 140 | 140 | 66 | 835 |

The 2.9% by weight of glycerin were added as a softener. The 0.7% by weight of polyethylenglycol were added as a plasticizer.

The 1.3% by weight of calcium-stearate were added as a lubricant.

The 44.9% by weight of hydorxypropylmethyl-cellulose were added as an extender.

The resulting capsules have enteric properties (2 hours resistance in gastric juice, soluble within well 30 minutes in intestinal juice according to USP XX).

EXAMPLE 8

A batch of HPMCP with a certain content of water (and glycerin, polyethylenglycol, calcium-stearate and hydroxypropylmethyl-cellulose) was prepared and conditioned and then tested in an injection molding machine. A batch of HPMCP in powdered form was conditioned as follows: The HPMCP of which the water content was 2% and the other additives were filled into a drum and sprayed with a specially fine spray of water to the calculated content as wanted. The batch was then thoroughly mixed and stored in the closed drum for half a day at ambient temperature. Acceptable gelatin capsules were then produced according to the working conditions listed on Table 8 below:

TABLE 8

| Material Composition: | HPMCP: 73.9%; glycerin: 5.3%; PE-glycol (10.000): 1.3%; Ca—stearate: 2.5%; HPMC: 9.2%; water: 7.8% | | | | |
|---|---|---|---|---|---|
| $T_b$ | $T_m$ | $T_e$ | $T_g$ | L/D | LFV |
| 110 | 125 | 135 | 135 | 66 | 860 |

The 5.3% by weight of glycerin were added as a softener. The 1.3% by weight of polyethyleglycol were added as a plasticizer.

The 2.5% by weight of calcium-stearate were added as a lubricant.

The 9.2% by weight of hydroxypropylmethy-cellulose were added as an extender.

The resulting capsules have enteric properties (2 hours resistance in gastric juice, soluble within well 30 minutes in intestinal juice according to USP XX).

EXAMPLE 9

A batch of HPMCP with a certain content of water (and glycerin, polyethylenglycol, calcium-stearate and soy protein) was prepared and conditioned and then tested in an injection molding machine. A batch of HPMCP in powdered form was conditioned as follows:

The HPMCP of which the water content was 2% and the other additives were filled into a drum and sprayed with a specially fine spray of water to the calculated content as the closed drum for half a day at ambient temperature. Acceptable gelatin capsules were then produced according to the working conditions listed on Table 9 below:

TABLE 9

| Material Composition: | HPMCP: 40%; glycerin: 2.9%; PE-glycol (10.000): 0.7%; Ca—stearate: 1.3%; soy protein: 44.9%; water: 10.2% | | | | |
|---|---|---|---|---|---|
| $T_b$ | $T_m$ | $T_e$ | $T_g$ | L/D | LFV |
| 110 | 120 | 140 | 140 | 66 | 840 |

The 2.9% by weight of glycerin were added as softener. The 0.7% by weight of polyethylenglycol were added as a plasticizer.

The 1.3% by weight of calcium-stearate were added as a lubricant.

The 44.9% by weight of soy protein were added as an extender. The resulting capsules have enteric properties (2 hours resistance in gastric juice, soluble within well 30 minutes in intestinal juice according to USP XX).

EXAMPLE 10

A batch of HPMCP with a certain content of water (and glycerin, polyethylenglycol, calcium-stearate and soy protein) was prepared and conditioned and then tested in an injection molding machine. A batch of HPMCP in powdered form was conditioned as follows:

The HPMCP of which the water content was 2% and the other additives were filled into a drum and sprayed with a specially fine spray of water to the calculated content as wanted. The batch was then thoroughly mixed and stored in the closed drum for half a day at ambient temperature. Acceptable gelatin capsules were then produced according to the working conditions listed on Table 10 below:

TABLE 10

| Material Composition: | HPMCP: 74.3%; glycerin: 5.3%; PE-glycol (10.000): 1.3%; Ca—stearate: 2.5%; soy protein: 9.4%; water: 7.2% | | | | |
|---|---|---|---|---|---|
| $T_b$ | $T_m$ | $T_e$ | $T_g$ | L/D | LFV |
| 110 | 125 | 135 | 135 | 66 | 1400 |

The 5.3% by weight of glycerin were added as a softener. The 1.3% by weight of polyethylenglycol were added as a plasticizer.

The 2.5% by weight of calcium-stearate were added as a lubricant.

The 9.4% by weight of soy protein were added as an extender. The resulting capsules have enteric properties (2 hours resistance in gastric juice, soluble within well 30 minutes in intestinal juice according to USP XX).

EXAMPLE 11

A batch of HPMCP with a certain content of water (and glycerin, polyethylenglycol, calcium-stearate and polyvinylpyrrolidone) was prepared and conditioned and then tested in an injection molding machine. A batch of HPMCP in powdered form was conditioned as follows:

The HPMCP of which the water content was 2% and the other additives were filled into a drum and sprayed with a specially fine spray of water to the calculated content as wanted. The batch was then thoroughly mixed and stored in the closed drum for half a day at ambient temperature. Acceptable capsules were then produced according to the working conditions listed on Table 11 below:

TABLE 11

| Material Composition: | HPMCP: 38.7%; glycerin: 2.8%; PE-glycol (10.000): 0.7%; Ca—stearate: 1.3%; polyvinylpyrrolidone: 45.3%; water: 13.0% | | | | |
|---|---|---|---|---|---|
| $T_b$ | $T_m$ | $T_e$ | $T_g$ | L/D | LFV |
| 120 | 140 | 140 | 140 | 66 | 830 |

The 2.8% by weight of glycerin were added as a softener.

The 0.7% by weight of polyethylenglycol were added as a plasticizer.

The 1.3% by weight of calcium-stearate were added as a lubricant.

The 43.5% by weight of polyvinylpyrrolidone were added as an extender.

The resulting capsules have enteric properties (2 hours resistance in gastric juice, soluble within well 30 minutes in intestinal juice according to USP XX).

EXAMPLE 12

A batch of gum arabic with a certain content of water was prepared and conditioned and then tested in an injection molding machine. The batch of gum arabic in powdered form was conditioned as follows:

The gum arabic of which the water content was 10.8% was filled into a drum and sprayed with a specially fine spray of water to the calculated content as wanted. The batch was then thoroughly mixed and stored in the closed drum for half a day at ambient temperature. Acceptable capsules were then produced according to the working conditions listed on Table 12 below:

TABLE 12

| Material Composition: | HPMCP: 38.7%; glycerin: 2.8%; PE-glycol (10.000): 0.7%; Ca—stearate: 1.3%; polyvinylpyrrolidone: 45.3%; water: 13.0% | | | | |
|---|---|---|---|---|---|
| $T_b$ | $T_m$ | $T_e$ | $T_g$ | L/D | LFV |
| 75 | 105 | 112 | 130 | 66 | 800 |

EXAMPLE 13

A batch of methylcellulose with a certain content of water was prepared and conditioned and then tested in an injection molding machine. The batch of methylcellulose in powdered form was conditioned as follows:

The methylcellulose of which the water content was 6.6% was filled into a drum and sprayed with a specially fine spray of water to the calculated content as wanted. The batch was then thoroughly mixed and stored in the closed drum for half a day at ambient temperature. Acceptable gelatin capsules were then produced according to the working conditions listed on Table 13 below:

TABLE 13

| Material Composition: | methylcellulose: 81.2%; water: 18.8% | | | | |
|---|---|---|---|---|---|
| $T_b$ | $T_m$ | $T_e$ | $T_g$ | L/D | LFV |
| 84 | 129 | 149 | 161 | 66 | 800 |

EXAMPLE 14

A batch of polyvinylpyrrolidone with a certain content of water was prepared and then tested in an injection molding machine. The batch of polyvinylpyrrolidone in powdered form was conditioned as follows:

The polyvinylpyrrolidone of which the water content was 16.8% was filled into a drum and sprayed with a specially fine spray of water to the calculated content as wanted. The batch was then thoroughly mixed and stored in the closed drum for half a day at ambient temperature. Acceptable capsules were then produced according to the working conditions listed on Table 14 below:

TABLE 14

| Material Composition: | polyvinylpyrrolidone: 81%; water: 19% | | | | |
|---|---|---|---|---|---|
| $T_b$ | $T_m$ | $T_e$ | $T_g$ | L/D | LFV |
| 85 | 130 | 135 | 135 | 66 | 800 |

EXAMPLE 15

A batch of cellulose acetate phthalate with a certain content of water was prepared and then tested in an injection molding machine. The batch of cellulose acetate phthalate powdered form was conditioned as follows:

The cellulose acetate phthalate of which the water content was 5.1% was filled into a drum and sprayed with a specially fine spray of water to the calculated content as wanted. The batch was then thoroughly mixed and stored in the closed drum for a half a day at ambient temperature. Acceptable capsules were then produced according to the working conditions listed on Table 15 below:

TABLE 15

| Material Composition: | cellulose acetate phthalate: 81%; water: 19% | | | | |
|---|---|---|---|---|---|
| $T_b$ | $T_m$ | $T_e$ | $T_g$ | L/D | LFV |
| 90 | 130 | 140 | 145 | 66 | 800 |

I claim:

1. A non gelatin based hydrophilic polymer-water composition having no phase separation of water from the hydrophilic polymer-water mixture at a water content of between about 5 and 25% by weight of the hydrophilic polymer, said hydrophilic polymer selected from a class consisting of hydroxymethylcellulose, gum arabic, methylcellulose, polyvinylpyrrolidone, cellulose acetate phthalate, water soluble ethers and esters derived therefrom, and mixtures thereof, said mixture being obtained by:
   (a) mixing the polymer with water in a predetermined amount between about 5 and 25% by weight of the hydrophilic polymer;
   (b) heating the hydrophilic polymer with said water while maintaining said predetermined water content to form a melt; and
   (c) further heating the hydrophilic polymer in water mixture above its glass transition temperature and above its melting point to dissolve the melt in the water and achieve a melt as a molecularly dispersed solution.

2. The composition of claim 1 wherein the composition is formed into a capsule and subjected to a minimal deformation during forming.

3. The composition of claim 1 wherein the water is present in a level of about 10 to about 20% by weight of the polymer.

4. The composition of claim 1 wherein a crosslinking agent is added just prior to pressure molding.

5. The composition of claim 1 wherein a plasticizing agent is present.

6. The composition of claim 1 wherein a lubricating agent is present.

7. The composition of claim 1 wherein a coloring agent is present.

* * * * *